United States Patent
Zuber et al.

(10) Patent No.: US 10,791,760 B2
(45) Date of Patent: Oct. 6, 2020

(54) AEROSOL-GENERATING SYSTEM INCLUDING A CARTRIDGE CONTAINING A GEL

(71) Applicant: Altria Client Services LLC, Richmond, VA (US)

(72) Inventors: Gerard Zuber, Froideville (CH); Jean-Yves Vollmer, Fontaines sur Grandson (CH)

(73) Assignee: Altria Client Services LLC, Richmond, VA (US)

( * ) Notice: Subject to any disclaimer, the term of this patent is extended or adjusted under 35 U.S.C. 154(b) by 373 days.

(21) Appl. No.: 15/662,438

(22) Filed: Jul. 28, 2017

(65) Prior Publication Data

US 2018/0027883 A1 Feb. 1, 2018

Related U.S. Application Data

(63) Continuation of application No. PCT/EP2017/067449, filed on Jul. 11, 2017.

(30) Foreign Application Priority Data

Jul. 29, 2016 (EP) .................................. 16181953

(51) Int. Cl.
*A24F 47/00* (2020.01)
*A61M 15/06* (2006.01)
(Continued)

(52) U.S. Cl.
CPC ....... *A24F 47/008* (2013.01); *A61M 15/0028* (2013.01); *A61M 15/06* (2013.01);
(Continued)

(58) Field of Classification Search
CPC ...... A24F 47/008; A24F 47/002; A24F 47/00; A24F 47/02; A24F 47/04; A24D 1/14; A61M 11/04; A61M 15/002; A61M 15/06
See application file for complete search history.

(56) References Cited

U.S. PATENT DOCUMENTS 4,126,239 A * 11/1978 Gehrig .................... F42B 3/00
                                                            206/3
2013/0167853 A1    7/2013 Liu
(Continued)

FOREIGN PATENT DOCUMENTS

CN       103960784 A    8/2014
CN       104256888 A    1/2015
(Continued)

OTHER PUBLICATIONS https://www.ecig-vapo.com/e-solid-ice-mint-p-105.html, retrieved on Dec. 12, 2018.
(Continued)

*Primary Examiner* — Samchuan C Yao
*Assistant Examiner* — Margaret M Luarca
(74) *Attorney, Agent, or Firm* — Harness, Dickey & Pierce, P.L.C.

(57) ABSTRACT

A cartridge for an aerosol-generating system may include a first chamber housing defining a first chamber and a second chamber housing defining a second chamber that is separate from the first chamber. The first chamber may contain an aerosol-forming substrate in the form of a gel, and the second chamber may contain a source of a desired compound. The first and second chamber housings may be separate or separable structures.

20 Claims, 8 Drawing Sheets

(51) Int. Cl.
  *H05B 1/02* (2006.01)
  *H05B 6/10* (2006.01)
  *H05B 3/34* (2006.01)
  *H05B 3/26* (2006.01)
  *A61M 15/00* (2006.01)
  *A61M 11/04* (2006.01)

(52) U.S. Cl.
  CPC ........... *H05B 1/0244* (2013.01); *H05B 3/265* (2013.01); *H05B 3/34* (2013.01); *H05B 6/108* (2013.01); *A61M 11/042* (2014.02); *A61M 15/0021* (2014.02); *A61M 15/0035* (2014.02); *A61M 2205/0211* (2013.01); *A61M 2205/8206* (2013.01); *H05B 2203/021* (2013.01)

(56) References Cited

U.S. PATENT DOCUMENTS

| | | | |
|---|---|---|---|
| 2014/0060554 A1 | 3/2014 | Collett et al. | |
| 2014/0060556 A1 | 3/2014 | Liu | |
| 2014/0209105 A1 | 7/2014 | Sears et al. | |
| 2014/0366898 A1 | 12/2014 | Monsees et al. | |
| 2016/0120224 A1 | 5/2016 | Mishra et al. | |
| 2016/0143360 A1 | 5/2016 | Sanchez et al. | |
| 2017/0340005 A1* | 11/2017 | Terao | A24B 15/167 |
| 2018/0199628 A1* | 7/2018 | Sheng | B05B 7/1686 |

FOREIGN PATENT DOCUMENTS

| | | | | |
|---|---|---|---|---|
| EP | 0509657 A1 | 10/1992 | | |
| EP | 2279677 A1 | 2/2011 | | |
| EP | 2550877 A1 | 1/2013 | | |
| EP | 2424392 B1 | 4/2013 | | |
| EP | 2488054 B1 | 12/2013 | | |
| EP | 2741626 A1 | 6/2014 | | |
| EP | 2787846 A1 | 10/2014 | | |
| EP | 3435798 A1 | 2/2019 | | |
| WO | WO-00/28842 A1 | 5/2000 | | |
| WO | WO-2009/079641 A2 | 6/2009 | | |
| WO | WO-2013/126167 A1 | 8/2013 | | |
| WO | WO-2013/128176 A1 | 9/2013 | | |
| WO | WO-2014/201432 A1 | 12/2014 | | |
| WO | WO-2015011569 A2 | 1/2015 | | |
| WO | WO-2015/038981 A2 | 3/2015 | | |
| WO | WO-2015/073564 A1 | 5/2015 | | |
| WO | WO-2015101479 A1 * | 7/2015 | ............. | A24B 15/16 |
| WO | WO-2015177043 A1 * | 11/2015 | ........... | H05B 1/0244 |
| WO | WO-2015/197627 A1 | 12/2015 | | |
| WO | WO-2016/046362 A1 | 3/2016 | | |
| WO | WO-2016135342 A2 * | 9/2016 | ............ | A61M 15/06 |

OTHER PUBLICATIONS

Extended European Search Report for European Application No. 16181953.7 dated Jan. 25, 2017.
Written Opinion for corresponding International No. PCT/EP2017/067449 dated Jul. 4, 2018.
International Search Report and Written Opinion for corresponding International Application No. PCT/EP2017/067449 dated Oct. 9, 2017.
International Preliminary Report on Patentability dated Nov. 20, 2018 for corresponding International Application No. PCT/EP2017/067449.
European Office Action dated Feb. 26, 2020 for corresponding European Application No. 17736965.9.

* cited by examiner

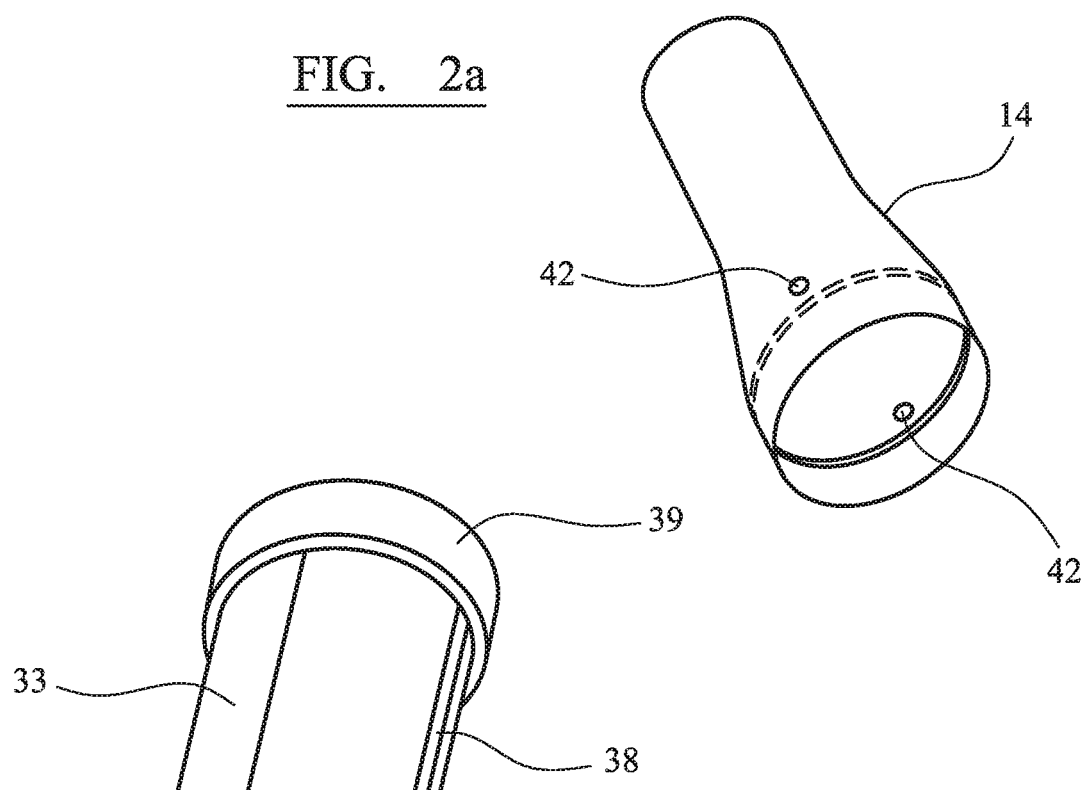
FIG. 2a
FIG. 2b
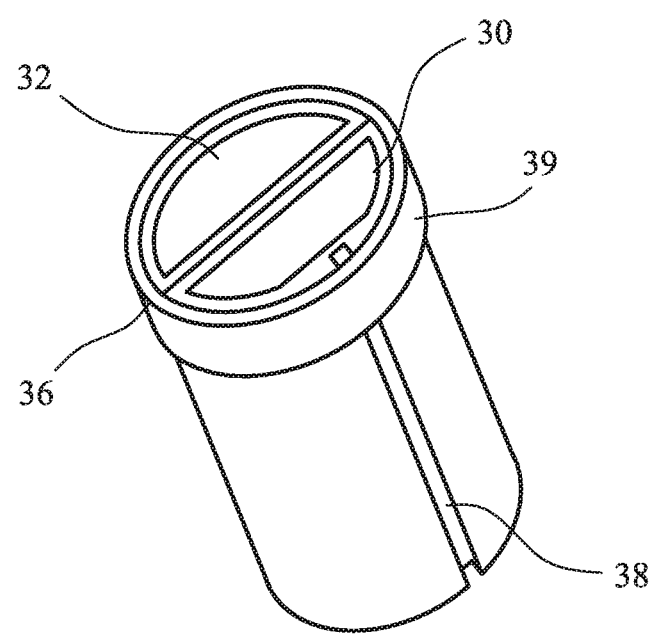
FIG. 2c

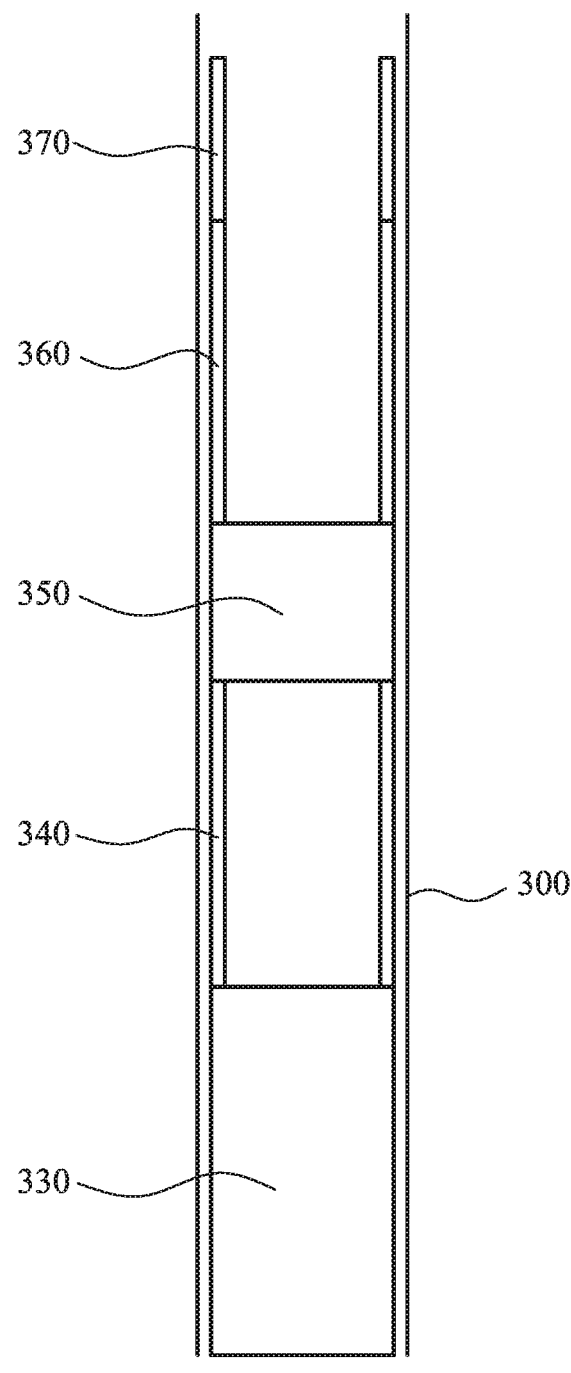
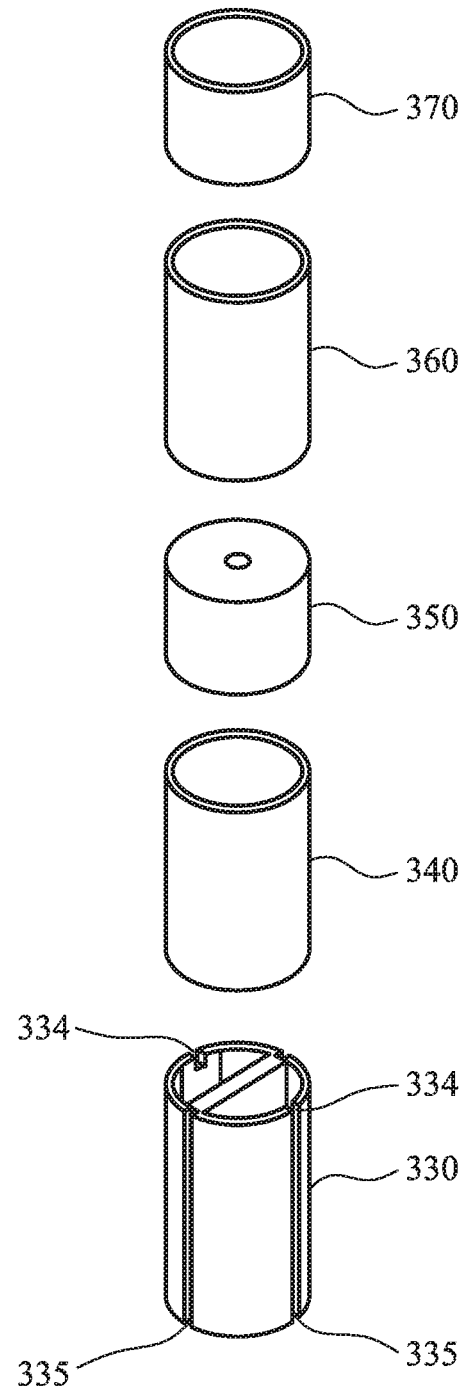
FIG. 6a
FIG. 6b

AEROSOL-GENERATING SYSTEM INCLUDING A CARTRIDGE CONTAINING A GEL

CROSS-REFERENCE TO RELATED APPLICATIONS

This is a continuation of and claims priority to PCT/EP2017/067449, filed on Jul. 11, 2017, and further claims priority to EP 16181953.7, filed on Jul. 29, 2016, both of which are hereby incorporated by reference in their entirety.

BACKGROUND

Field

Example embodiments relate to an aerosol-generating system that heats an aerosol-forming substrate to generate an aerosol, including an aerosol-generating system that heats a gel to form an aerosol.

Description of Related Art

Aerosol-generating systems operate by heating a liquid formulation to generate an aerosol. Typically, aerosol-generating systems comprise a device portion and a cartridge. In some systems, the device portion contains a power supply and control electronics, and the cartridge contains a liquid reservoir holding the liquid formulation, a heater for vaporizing the liquid formulation, and a wick that transports the liquid from the liquid reservoir to the heater. However, there is a potential for leakage of the liquid from the liquid reservoir both during transport and storage, and when the cartridge is connected to the device portion. The use of a wick to transport the liquid from the reservoir to the heater may also add complexity to the system.

SUMMARY

A cartridge for an aerosol-generating system may comprise a first chamber housing defining a first chamber and a second chamber housing defining a second chamber that is separate from the first chamber. The first chamber may be configured to contain an aerosol-forming substrate in a form of a first gel. The second chamber may be configured to contain a source of a desired compound. The first chamber housing and the second chamber housing may be separate or separable structures.

The first gel may include a thermoreversible gel.

The first chamber housing and the second chamber housing may be connected by a mechanical interlock or by a fastening element.

The first gel may include agar, agarose, Gellan gum, or sodium alginate.

The source of the desired compound may include a nicotine source or a flavour source.

The second chamber may be configured to contain a second gel, and the second gel may include the source of the desired compound.

The first chamber may also be configured to contain a nicotine source.

The second chamber may be configured to contain a solid tobacco material.

The first chamber housing and the second chamber housing may define a slot therebetween.

The slot may be a blind slot.

The first chamber and the second chamber may contain different compositions.

The first chamber and the second chamber may be blind chambers.

At least one of the first chamber housing and the second chamber housing may include a susceptor layer.

An aerosol-generating system may comprise a cartridge and a device body. The device body may include a power supply configured to apply a voltage to an electrical heater. The cartridge may be configured to removably connect to or be removably received in the device body.

The electrical heater may be configured to heat the cartridge to generate a vapour. The electrical heater may not be in direct contact with the aerosol-forming substrate.

The electrical heater may be configured to heat the aerosol-forming substrate within the first chamber housing.

The device body may include the power supply and the electrical heater. The electrical heater may be positioned between the first chamber and the second chamber when the cartridge is connected to or received in the device body.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 2a is a perspective view of a mouthpiece portion in accordance with an example embodiment.

FIG. 2b is a bottom perspective view of a cartridge housing in accordance with an example embodiment.

FIG. 2c is a top perspective view of the cartridge assembly of FIG. 2b.

FIG. 6a is a schematic illustration of a cartridge assembly that is held within a mouthpiece tube in accordance with an example embodiment.

FIG. 6b is an exploded view of the elements within the mouthpiece tube of FIG. 6a.

FIG. 7 is an illustration of the airflow through the mouthpiece tube of FIG. 6a.

DETAILED DESCRIPTION

Figure 1:
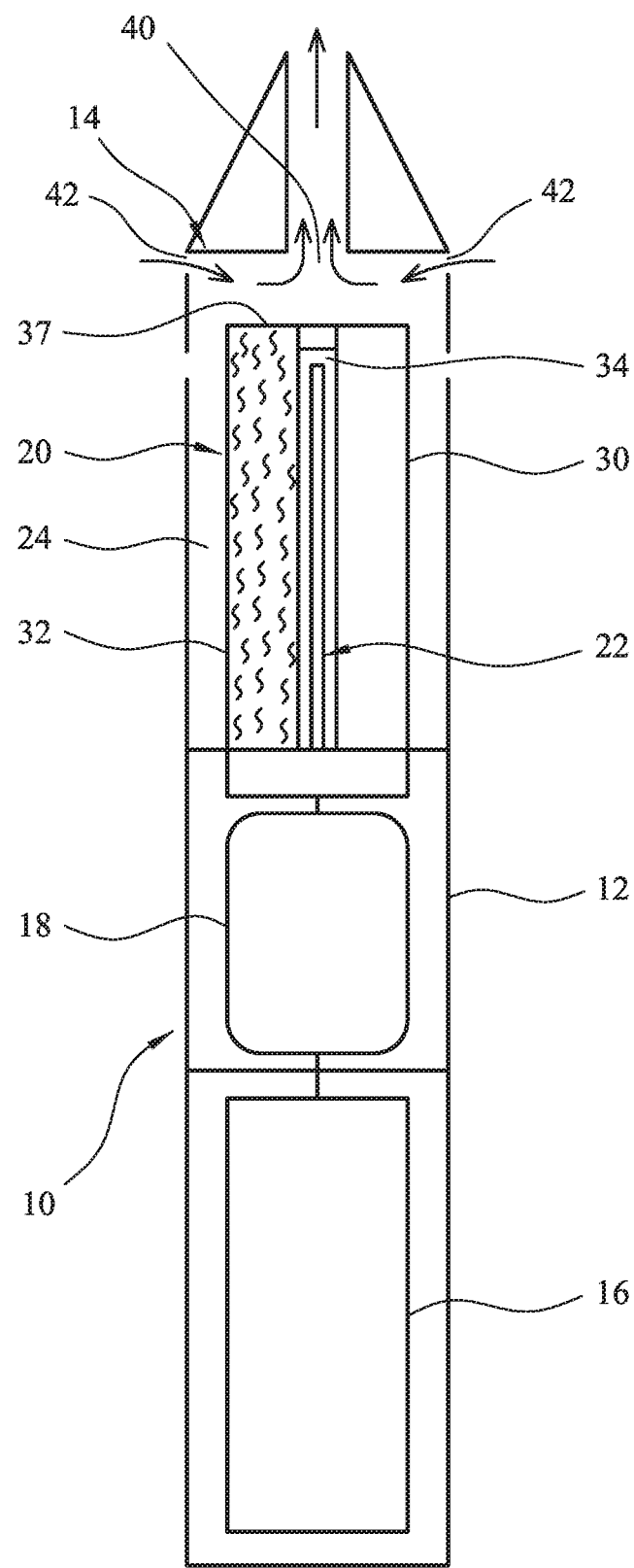
FIG. 1 is a schematic illustration of an aerosol-generating system in accordance with an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments, there is provided an aerosol-generating cartridge for an aerosol-generating system. The aerosol-generating cartridge may comprise a first chamber and a second chamber that is separate from the first chamber. The first chamber may contain an aerosol-forming substrate in the form of a gel, and the second chamber may contain a source of a desired compound.

The source of a desired compound may comprise one or both of a source of nicotine and a flavour source.

The gel may be solid at room temperature. "Solid" in this context means that the gel has a stable size and shape and does not flow. The first and second chambers may contain different compositions. Both the first and second chambers may contain a gel. The second chamber may contain a solid material. In an example embodiment, neither the first chamber nor the second chamber contains a material which is not solid at room temperature.

In this context, an aerosol-forming substrate is a material or mixture of materials capable of releasing volatile compounds that can form an aerosol. The provision of the aerosol-forming substrate in the form of a gel may be beneficial for storage and transport. By providing the aerosol-forming substrate in a gel, the risk of leakage from the device may be reduced. Replenishing of the device with aerosol forming substrate when depleted or exhausted may also be improved, for example by reducing the risk of leakage or spillage.

The aerosol-forming substrate may comprise an aerosol-former. As used herein, the term "aerosol-former" refers to any suitable known compound or mixture of compounds that, in use, facilitates formation of a dense and stable aerosol. An aerosol-former is substantially resistant to thermal degradation at the operating temperature of the cartridge. Suitable aerosol-formers are known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. In an example embodiment, the aerosol formers are polyhydric alcohols or mixtures thereof, such as triethylene glycol, 1,3-butanediol, and glycerine or polyethylene glycol.

A gel formulation or composition that is suited to releasing aerosol-former at a particular temperature may not be ideally suited for retaining and then releasing other compounds. By providing separate chambers, one containing the aerosol-former and one or more others containing the other compounds, for example nicotine or flavour source compounds, improved retention and release for both can be realised.

The first chamber may contain additional materials or components in addition to the gel.

As used herein, the term "aerosol-generating cartridge" refers to an article comprising an aerosol-forming substrate that is intended to be heated rather than combusted in order to release volatile compounds that can form an aerosol. When the resulting aerosol is to contain nicotine, a source of the nicotine may be contained in a gel. The source of nicotine may be included in one or both of the first and second chambers. The nicotine may be included in a gel with an aerosol-former in the first chamber or may be included in a second gel in the second chamber or may be included in gels in both chambers. Reducing the risk of leakage of nicotine-containing material from the system by retaining the nicotine in the gel at room temperature is therefore desirable. In alternative arrangements, the source of nicotine may be housed in the second chamber, for example in a liquid or solid material.

Flavour compounds may be contained in the second chamber in a gel. Alternatively or in addition, flavour compounds may be provided in another form. For example, the second chamber may contain a solid tobacco material that releases flavour compounds when heated. The second chamber may contain, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid tobacco material in the second chamber may be in loose form. The tobacco may be contained in a gel or liquid. The second chamber may contain additional tobacco or non-tobacco volatile flavour compounds, to be released upon heating.

The first or second chamber may contain capsules that, for example, include volatile flavour compounds and such capsules may release their content, for example by melting during heating.

The gel may comprise a thermoreversible gel. This means that the gel will become fluid when heated to a melting temperature and will set into a gel again at a gelation temperature. The gelation temperature may be at or above room temperature and atmospheric pressure. Room temperature in this context means 25 degrees Celsius. Atmospheric pressure means a pressure of 1 atmosphere. The melting temperature is higher than the gelation temperature. The melting temperature of the gel may be above 50 degrees Celsius (e.g., above 60 degrees Celsius, above 70 degrees Celsius, or above 80 degrees Celsius). The melting temperature in this context means the temperature at which the gel is no longer solid and begins to flow. In a non-limiting embodiment, the gel comprises agar or agarose or sodium alginate. The gel may comprise Gellan gum. The gel may comprise a mixture of materials. The gel may comprise water.

The gel may be provided as a single block or may be provided as a plurality of gel elements, for example beads or capsules. The use of beads or capsules may allow for simple refilling of the first (or second) chamber. The use of capsules or beads may also allow a visual indication as to when a cartridge has already been used, because gel will not form the same capsules or beads on gelation after heating and subsequent cooling.

When agar is used as the gelling agent, the gel may comprise between 0.5 and 5% by weight (e.g., between 0.8 and 1% by weight) agar. The gel may further comprise between 0.1 and 2% by weight nicotine. The gel may further comprise between 30% and 90% by weight (e.g., between 70 and 90% by weight) glycerin. A remainder of the gel may comprise water and any flavourings.

When Gellan gum is used as the gelling agent, the gel may comprise between 0.5 and 5% by weight Gellan gum. The gel may further comprise between 0.1 and 2% by weight nicotine. The gel may further comprise between 30% and 99.4% by weight glycerin. A remainder of the gel may comprise water and any flavourings.

In an example embodiment, the gel comprises 2% by weight nicotine, 70% by weight glycerol, 27% by weight water, and 1% by weight agar. In another example embodiment, the gel comprises 65% by weight glycerol, 20% by weight water, 14.3% by weight tobacco, and 0.7% by weight agar.

In an example embodiment, the cartridge does not comprise a transport element or mechanism for transporting the aerosol-former to a heat source or heater. For instance, the contents of the first or second chambers may be heated in situ to generate a desired aerosol. In this context, in situ means in the same position within the first and second chambers that the contents are held prior to the heating to generate the aerosol. Thus, there is no requirement for a capillary wick or pump in such an example. Furthermore, in a non-limiting embodiment, neither the first chamber nor the second chamber comprises a non-volatile structure for holding or retaining a liquid or gel in proximity to the heater.

The first and second chambers may be positioned side by side or one within the other or may be arranged in series such that an air flow can pass first through or past one chamber and then through or past the other.

The cartridge may comprise a slot between the first and second chambers. The slot may be configured to receive a heating element. The heating element may be received in the slot for example when the cartridge is installed in an aerosol-forming device. The provision of a slot into which a heating element is received may provide for efficient heating by facilitating that heat energy from the heating element is passed directly to the first and second chambers rather than for example heating other elements of the system or the ambient air. The slot may be a blind slot. "Blind" in this context means closed at one end. The provision of a blind slot allows the heating element to be shielded from the vapour or aerosol generated by the system and can help to prevent the build-up of condensates on the heater.

The cartridge may be referred to as a cartridge assembly and may comprise chambers that can be separately inserted into, or connected to, and removed from, other elements of the aerosol-generating system. The cartridge assembly may comprise components in addition to the first and second chambers. The cartridge may comprise a housing. The housing of the cartridge may be formed from one or more materials. Suitable materials include, but are not limited to, metal, aluminium, polymer, polyether ether ketone (PEEK), polyimides, such as Kapton®, polyethylene terephthalate (PET), polyethylene (PE), polypropylene (PP), polystyrene (PS), fluorinated ethylene propylene (FEP), polytetrafluoroethylene (PTFE), epoxy resins, polyurethane resins and vinyl resins.

The housing of the cartridge may be formed from one or more thermally conductive materials. The interior of the first chamber or the second chamber may be coated or treated to comprise one or more thermally conductive materials. Use of one or more thermally conductive materials to form the cartridge or coat the interior of the first chamber and the second chamber may increase heat transfer from the heater to the content of the chamber, for example the gel. Suitable thermally conductive materials include, but are not limited to, metals such as, for example, aluminium, chromium, copper, gold, iron, nickel and silver, alloys, such as brass and steel and ceramics, or combinations thereof. At least one wall of the housing may have a thermal conductivity greater than 10 Watts per metre per Kelvin at room temperature. In an example embodiment, the housing comprises a least one wall formed from aluminium.

In example embodiments in which the cartridge is configured to be heated inductively, the housing of the cartridge may comprise a susceptor, for example a susceptor layer. The susceptor layer may for example form a wall of the housing or may be a coating applied to the interior or exterior of the housing. A susceptor may be located within the first or second chambers. For example, the gel may comprise a susceptor material.

Cartridges for use in aerosol-generating systems may be formed by any suitable method. Suitable methods include, but are not limited to, deep drawing, injection moulding, blistering, blow forming, and extrusion.

The cartridge may comprise a mouthpiece configured to allow an application of a negative pressure to draw the aerosol from the aerosol-generating device. Where the cartridge comprises a mouthpiece, the mouthpiece may comprise a filter. The filter may have a low particulate filtration efficiency or very low particulate filtration efficiency. Alternatively, the mouthpiece may comprise a hollow tube. The mouthpiece may comprise an airflow modifier, for example a restrictor.

The cartridge may be provided within a mouthpiece tube. The mouthpiece tube may comprise an aerosol-forming chamber. The mouthpiece tube may comprise an airflow restrictor. The mouthpiece tube may comprise a filter. The mouthpiece tube may comprise a cardboard housing. The mouthpiece tube may comprise one or more vapour impermeable elements within the cardboard tube. The mouthpiece tube may have a diameter similar to a cigarette, for example around 7 mm. The mouthpiece tube may have an end through which the aerosol exits. The cartridge may be held in the mouthpiece tube for example at an opposite end to the mouth end.

One or both of the first and second chambers may be blind chambers. Blind in this context means closed at one end. In an example embodiment, there is only one exit aperture from the chamber. The cartridge housing may comprise at least one liquid and vapour impermeable external wall defining a blind chamber. Both the first and second chambers may be blind chambers. The use of blind chambers may reduce the risk of leakage. One or both of the chambers may be sealed by one or more frangible barriers.

The one or more frangible barriers may be formed from any suitable material. For example, the one or more frangible barriers may be formed from a foil or film, for example comprising metal. Where the cartridge comprises one or more frangible barriers sealing one or both of the first chamber and the second chamber, the device body may further comprise a piercing member configured to rupture the one or more frangible barriers.

Alternatively or in addition, one or both of the first chamber and the second chamber may be sealed by one or more removable barriers. For example, one or both of the first chamber and the second chamber may be sealed by one or more peel-off seals.

The one or more removable barriers may be formed from any suitable material. For example, the one or more removable barriers may be formed from a foil or film, for example comprising a metal.

One or both of the first and second chambers may be sealed by a vapour permeable element, for example a membrane or mesh configured to allow the escape of vapour from the first or second chamber through the membrane or mesh. Alternatively one or both of the first and second chambers may be sealed by a pressure activated valve that allows for the release of vapour through the valve when a pressure difference across the valve exceeds a threshold pressure difference.

The first chamber and the second chamber may be fixed together but separable from one another. The first and second chambers may be provided separately and fixed together using a suitable mechanical interlock, such as a snap fitting or a screw fitting. Alternatively, the first and second chambers may be held together using a separate retaining or fixing element. Alternatively, the first and second chambers may remain separate during use.

By providing the first and second chambers separately, a "mix and match" type set of choices may be made available. The contents of the first chamber may provide a particular dosage of a target compound for delivery, such as nicotine or a particular density of aerosol, and a range of options may be made available. The contents of the second chamber may primarily provide flavour compounds, and a range of options for the second chamber may be available. An adult vaper can choose one chamber from the range of first chambers and one chamber from the range of second chambers and may fit them together to form a complete cartridge.

Even when the first and second chambers are provided together and permanently fixed to one another, the same mix and match approach may be taken by a manufacturer to provide a range of different cartridge assemblies.

The first and second chambers may be of the same size and shape as one another or they may have a different size or shape to one another. The size and shape of the first and second chamber may be chosen to suit their contents, and to provide for a particular heating rate in use.

It is also possible to have more than two chambers. It may be desirable to have three or more chambers in the cartridge assembly, with at least two of the chambers having different contents.

The cartridge may have any suitable shape.

In a non-limiting embodiment, the cartridge is substantially cylindrical.

The cartridge may have any suitable size.

The cartridge may have a length of, for example, between about 5 mm and about 30 mm. In some example embodiments, the cartridge may have a length of about 12 mm.

The cartridge may have a diameter of, for example, between about 4 mm and about 10 mm. In some example embodiments, the cartridge may have a diameter of about 7 mm.

An aerosol-generating system may comprise an aerosol-generating device and a cartridge according to any of the example embodiments described above. The aerosol-generating device may be an electrically operated aerosol-generating device. The aerosol-generating system may be configured to generate an aerosol. The aerosol-generating system may be a handheld system and may comprise a mouthpiece.

In an example embodiment, there is provided an aerosol-generating system comprising a cartridge comprising two separate chambers, one chamber containing an aerosol-forming substrate in the form of a gel, and the other containing a source of a desired compound, and an aerosol-generating device comprising a power supply for an electrical heater, the cartridge being configured to removably connect to or be removably received in the aerosol-generating device. Separate chambers may be connected to and removed from the aerosol-generating device separately. In some example embodiments, the cartridge is held within a mouthpiece tube, and the mouthpiece tube is removably received in the aerosol-generating device.

The source of a desired compound may comprise one or both of a source of nicotine and a flavour source.

The electrical heater may be configured to heat the cartridge to generate a vapour within the cartridge from the aerosol-forming substrate. The device body may comprise an electrical power supply and the electrical heater. Alternatively, the cartridge may comprise all or a portion of the electrical heater.

The aerosol-generating device of the aerosol-generating system may comprise: a housing having a cavity for receiving the cartridge. The aerosol-generating device may comprise electronic circuitry configured to control the supply of power from a power supply to an electric heating element of the electrical heater.

The electric heating element may comprise one or more heating elements.

In some example embodiments, the electrically operated aerosol-generating device comprises an electric heating element and a housing having a cavity, wherein the heated cartridge is received in the cavity. The heating element may conveniently be shaped as a needle, pin, rod, or blade that may be inserted into a slot or slots defined by the cartridge assembly.

The electric heating element may comprise one or more external heating elements, one or more internal heating elements, or one or more external heating elements and one or more internal heating elements. In this context, external means outside of the cavity and internal means inside of the cavity for receiving the cartridge.

The one or more external heating elements may comprise an array of external heating elements arranged around the inner surface of the cavity. In certain examples, the external heating elements extend along the longitudinal direction of the cavity. With this arrangement, the heating elements may extend along the same direction in which the cartridge is inserted into and removed from the cavity. This may reduce interference between the heating elements and the cartridge relative to devices in which the heating elements are not aligned with the length of the cavity. In some example embodiments, the external heating elements extend along the length direction of the cavity and are spaced apart in the circumferential direction. Where the heating element comprises one or more internal heating elements, the one or more internal heating elements may comprise any suitable number of heating elements. For example, the heating element may comprise a single internal heating element. The single internal heating element may extend along the longitudinal direction of the cavity.

The electric heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

The electric heating element may be formed using a metal having a defined relationship between temperature and resistivity. In such example embodiments, the metal may be formed as a track between two layers of suitable insulating materials. An electric heating element formed in this manner may be used both as a heater and a temperature sensor.

Where the electric heating element comprises a susceptor, the aerosol-generating device may comprise an inductor arranged to generate a fluctuating electromagnetic field within the cavity and an electrical power supply connected to the inductor. The inductor may comprise one or more coils that generate a fluctuating electromagnetic field. The coil or coils may surround the cavity.

The device may be capable of generating a fluctuating electromagnetic field of between 1 and 30 MHz. For example, the fluctuating electromagnetic field may be between 2 and 10 MHz (e.g., between 5 and 7 MHz). The device may be capable of generating a fluctuating electromagnetic field having a field strength (H-field) of between 1 and 5 kA/m. For example, the field strength may be between 2 and 3 kA/m (e.g., about 2.5 kA/m).

The aerosol-generating system and the aerosol-generating device according to an example embodiment may comprise a single heater. This configuration may simplify the device construction. The single heater may be configured as an external heater that in use is positioned externally to the cavity. Alternatively, the single heater may be configured as an internal heater that in use is positioned internally to the cavity and received in a slot in the cartridge. In a non-limiting embodiment, the single heater is configured as an internal heater.

Where the single heater is configured as an internal heater, the aerosol-generating device may comprise guide means to facilitate proper alignment of the internal heater with the cartridge.

The single heater may be an electric heating element comprising an electrically resistive material. The electric heating element may comprise a non-elastic material, for example, a ceramic sintered material, such as glass, alumina ($Al_2O_3$), and silicon nitride ($Si_3N_4$), or printed circuit board or silicon rubber. Alternatively, the electric heating element may comprise an elastic, metallic material, for example, an iron alloy or a nickel-chromium alloy.

The single heater may have any shape suitable to heat both chambers of the cartridge. The electrical heater may be positioned between the first and second chambers when the cartridge is connected to or received in the device body. In some example embodiments, the single heater is an elongate internal electric heating element. For instance, the single heater may be an elongate internal electric heating element having a width that is greater than the thickness thereof so that the elongate internal electric heating element is in the form of a heater blade.

In an example embodiment, the heater does not project from the aerosol-generating device.

The aerosol-generating system may comprise more than one heater to allow for different or selective heating of the first and second chambers. It may be desirable to heat the first chamber to a different temperature to the second chamber, for example.

The aerosol-generating system and the aerosol-generating device according to an example embodiment may further comprise one or more temperature sensors configured to sense the temperature of at least one of the electrical heater. In such example embodiments, the controller may be configured to control a supply of power to the electrical heater based on the sensed temperature.

Any suitable electronic circuitry may be used in order to control the supply of power to the electric heating element. The electronic circuitry may be a simple switch. Alternatively the electronic circuitry may comprise one or more microprocessors or microcontrollers. The electronic circuitry may be programmable.

The power supply may be a DC voltage source. In some example embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating cartridges.

The aerosol-generating device may comprise a body portion containing the power supply and a mouthpiece portion configured for engagement with the body portion. The body portion may be configured to receive the cartridge or cartridge assembly in a cavity of the body portion. By providing a reusable mouthpiece, separate to the cartridge, the construction of the cartridge can be simpler and relatively inexpensive.

The cavity of the aerosol-generating device may be substantially cylindrical.

As used herein, the terms "cylinder" and "cylindrical" refer to a substantially right circular cylinder with a pair of opposed substantially planar end faces.

The cavity of the aerosol-generating device may have a diameter substantially equal to or slightly greater than the diameter of the cartridge.

In an example embodiment, the system does not comprise a transport mechanism for transporting the aerosol-former to the heater. For instance, the contents of the cartridge may be heated in situ to generate a desired aerosol. In this context, in situ means in the same position within the first and second chambers that the contents are held prior to the heating to generate the aerosol. Thus, there is no requirement for a capillary wick or a pump in such an example.

Where the cartridge comprises one or more frangible barriers sealing one or both of the first chamber and the second chamber, the aerosol-generating device may further comprise a piercing member configured to rupture the one or more frangible barriers.

The aerosol-generating device may be a portable or handheld aerosol-generating device that is comfortable to hold between the fingers of a single hand.

The aerosol-generating device may be substantially cylindrical in shape. The aerosol-generating device may have a length of between approximately 70 millimetres and approximately 120 millimetres.

FIG. 1 is a schematic illustration of an aerosol-generating system in accordance with an example embodiment. The system comprises an aerosol-generating device 10 and a cartridge 20 (e.g., replaceable cartridge). The aerosol-generating device comprises a device body 12 and a mouthpiece portion 14.

The device body 12 comprises a power supply, which may be a battery 16 (e.g., lithium ion battery) and electronic control circuitry 18. The device body also includes heater 22, which is in the form a blade that projects into a cavity 24 in the housing of the device body. The heater is an electric heater comprising an electrically resistive track on a ceramic substrate material. The control circuitry is configured to control the supply of power from the battery 16 to the heater 22 (e.g., electric heater).

The mouthpiece portion 14 may engage the device body 12 using a relatively simple push fitting, although any type of suitable connection, such as a snap fitting or screw fitting may be used. The mouthpiece portion 14 may be a tapered hollow tube (e.g., without any filter elements) and is shown in more detail in FIG. 2a. However, it is possible to include one or more filter elements in the mouthpiece portion 14. The mouthpiece portion 14 comprises air inlet holes 42 and encloses an aerosol-forming chamber 40 (shown in FIG. 1) in which vapour can condense in an airflow prior to exiting the aerosol-generating device 10.

The cartridge 20 comprises a housing defining two blind chambers. The two chambers 30, 32 are open at a mouthpiece end. A membrane 37 (shown in FIG. 1) seals the open end of the chambers. A removable seal may be provided over the membrane and subsequently peeled off. A blind slot 34 is provided between the two chambers for the heater 22 to be received in. The blind slot 34 is closed at the mouthpiece end. A first chamber 30 holds a first gel, containing nicotine and aerosol-former, and the second chamber 32 holds a second gel, containing shredded tobacco leaves.

FIG. 2b is a bottom perspective view of the cartridge assembly housing. FIG. 2c is a perspective view of the cartridge assembly housing. The cartridge 20 has a generally cylindrical shape. The first chamber housing 35 and the second chamber housing 33 are separate and of equal size and shape, and held together at an interface 36. The first chamber housing 35 and the second chamber housing 33 are held together by a retaining ring 39. Both chamber housings engage the retaining ring 39. Other means of holding the chambers together are possible, such as a separate clip or bracket, or the provision of interlocking or snap fitting features on each of the chambers. The blind slot 34 is formed between the chambers when they are held together. A channel 38 is provided in a wall of the first chamber housing 35 to engage a corresponding rib in the cavity 24. In addition or in the alternative, the channel 38 may be provided in a wall of the second chamber housing 33. This ensures that the cartridge assembly can only be inserted into the cavity 24 in one orientation, in which the heater blade is received in the blind slot 34.

Figure 2D:
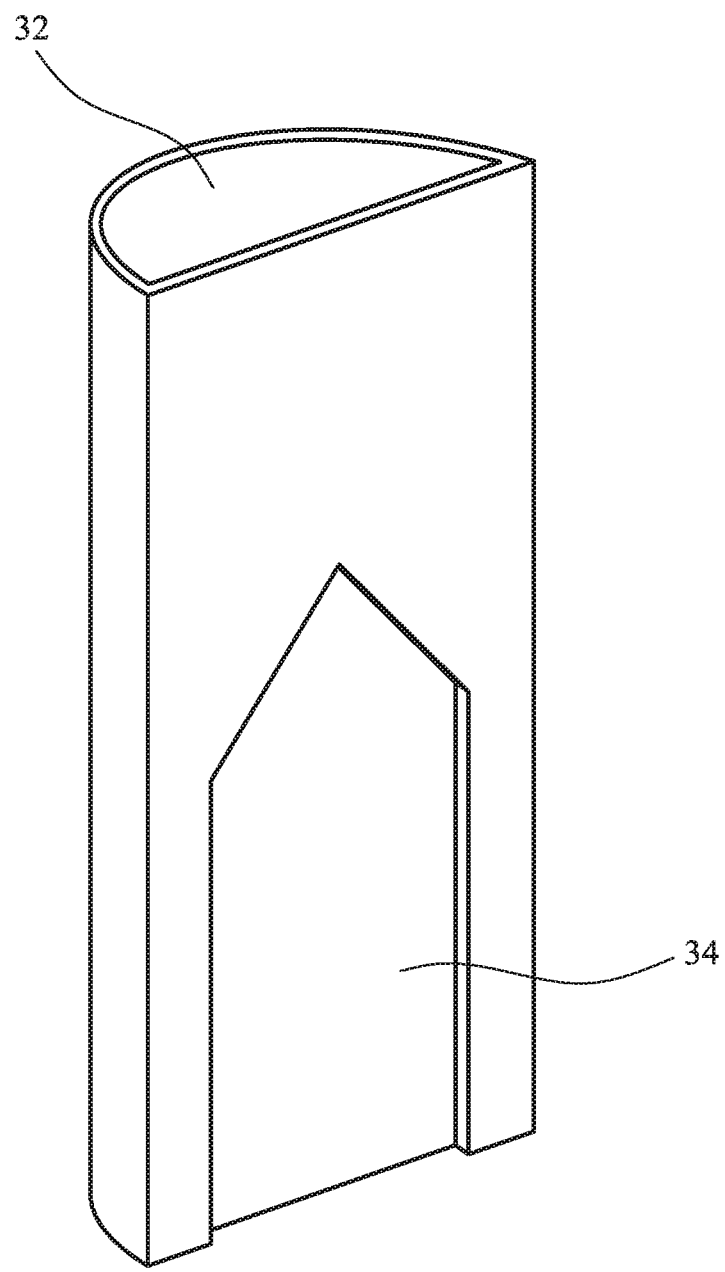
FIG. 2d shows one of the chambers of the cartridge assembly of FIG. 2b.

FIG. 2d shows the housing of one of the chambers shown in FIGS. 2b and 2c showing the shape of the blind slot 34. The shape of the slot matches the blade shape of the heater.

The first gel in the first chamber 30 comprises one or two aerosol formers such as glycerin and polyethylene glycol. The relative concentration of the aerosol formers can be adapted to the particular requirements of the system. In this example embodiment, the gel in the first chamber 30 comprises (by weight): 2% nicotine, 70% glycerin, 27% water, 1% agar.

The gelling agent may be agar, which has the property of melting at temperatures above 85° C. and turning back to gel at around 40° C. This property makes it suitable for relatively hot environments. For example, the gel will not melt at 50° C., which is useful if the system is left in a hot automobile in the sun. Also, a phase transition to liquid at around 85° C. means that the gel only needs to be heated to a relatively low-temperature to induce aerosolization, thus allowing a lower energy consumption. Furthermore, it may be beneficial to use only agarose, which is one of the components of agar, instead of agar.

The second gel in the second chamber 32 comprises (by weight): 65% glycerin, 20% water, 14.3% solid powdered tobacco, 0.7% agar Further or different flavors, such as menthol, can be added either in water or in propylene glycol or glycerin prior to the formation of the either of the gels.

The amount of gel provided in each cartridge can also be chosen to suit particular needs. For instance, each cartridge may contain enough gel to provide a single-occasion quantity for vaping or may contain sufficient gel for a multiple-occasion quantity for vaping.

In operation, the system is configured to operate in a continuous heating mode. This means that the heater 22 heats the cartridge throughout an operating session rather than in response to sensed puffs. The system can be turned on using a relatively simple switch (not shown) such that the heater heats the cartridge. A temperature sensor may be included in the system so that an indication can be provided as to when an operating temperature has been reached, at which an aerosol is generated. The gels become liquid upon heating above 85° C. Aerosol containing nicotine and glycerin is generated at temperatures between 180° C. to 250° C. During operation, the heater operates at approximately 250° C. The heater may operate for a fixed time period after activation (e.g., 6 minutes) or may operate until the system is switched off. The operating time may depend on the amount of gel contained within the cartridge.

The cartridge housing is formed of aluminium, which is a good thermal conductor. The heater is never in contact with the gel or any generated vapour or aerosol. It is held in the blind slot 34 and so is isolated from the generated aerosol. This ensures that there is no build-up of condensates on the heater, which might lead to the generation of undesirable compounds in operation.

FIGS. 3*a*, 3*ab*, and 3*c* illustrate an example embodiment in which each of the chambers of the cartridge is sealed by a frangible sealing element. The mouthpiece portion is used to pierce the sealing elements to allow vapour generated in the chambers to escape from the two chambers.

FIG. 3*a* illustrates the insertion of the cartridge 20 into the device body 12. As in FIG. 1, the cartridge comprises first and second chambers 30, 32 and a blind slot 34 between the chambers. The chambers are sealed by sealing elements 50.

FIG. 3*b* shows the cartridge inserted into the device, with the heater 22 received in the blind slot 34 between the chambers. A mouthpiece portion 14 is then connected to the device body 12. FIG. 3*b* illustrates the direction of insertion of the mouthpiece portion. The mouthpiece portion is provided with piercing elements 52 which acts to pierce the frangible sealing elements and provide an escape passage 54 for vapour generated in the first and second chambers.

FIG. 3*c* shows the mouthpiece portion 14 in a fully inserted position, with the piercing elements 52 extending into the first and second chambers and allowing vapour to escape from the first and second chambers 30, 32, into an aerosol-forming chamber in the mouthpiece portion. The vapour cools and is entrained in an airflow in the mouthpiece portion to form an aerosol. As in the example embodiment of FIG. 1, the mouthpiece portion may be provided with air inlets. Alternatively or in addition, an airflow path into the mouthpiece portion may be provided through the device. Alternatively or in addition, an airflow path may be provided through the first and second chambers.

Figure 4:
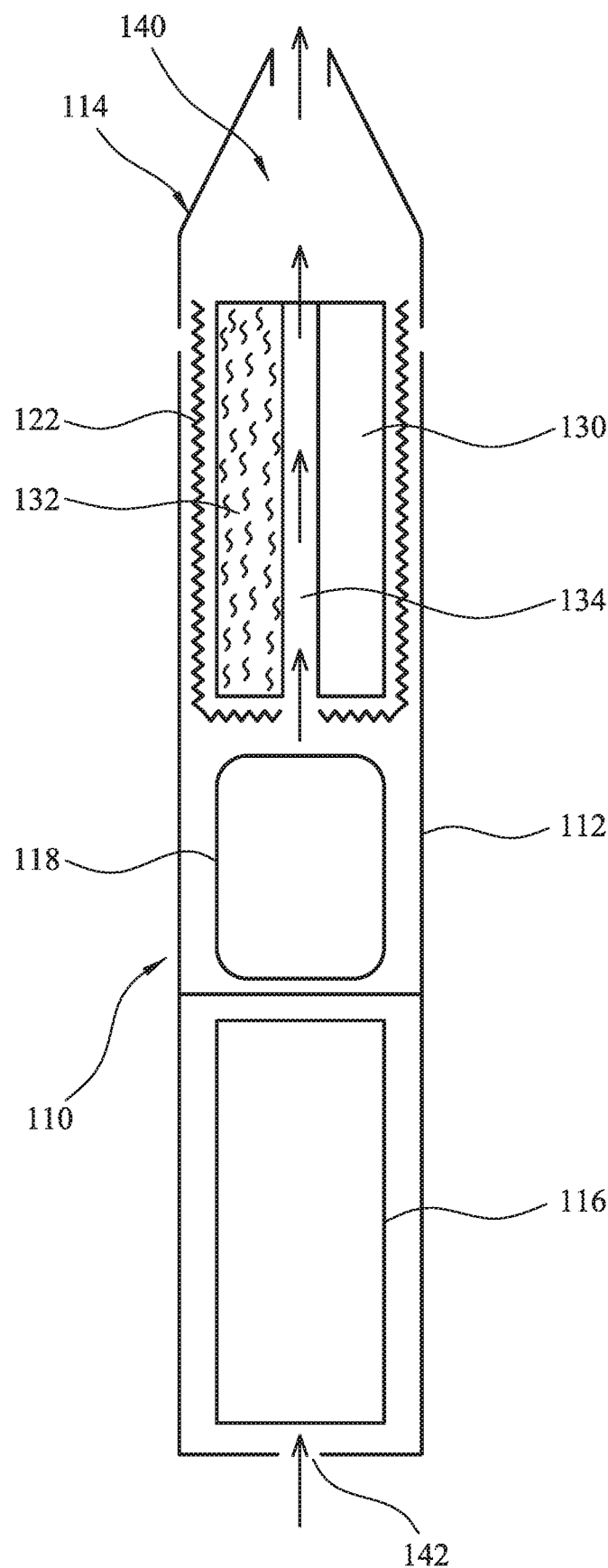
FIG. 4 is a schematic illustration of another aerosol-generating system in accordance with an example embodiment.

FIG. 4 is a schematic illustration of another aerosol-generating system in accordance with an example embodiment. In the example embodiment of FIG. 4, the aerosol-generating device 110 includes a heater 122 that is on the outside of the cavity of the device portion in which the cartridge assembly is received rather than extending into a slot formed in the cartridge assembly. The device body 112 comprises a power supply, which may be a battery 116 (e.g., lithium ion battery) and electronic control circuitry 118. The device body also includes a heater 122, which extends around a cavity in the housing of the device body. The heater is an electric heater comprising an electrically resistive track provided on a flexible substrate. Specifically, the heating element comprises a metallic etched foil forming a track, held between two layers of Kapton®. By providing a heater comprising electrically resistive tracks on a flexible substrate, the heater may be easier to manufacture and form into the required shape to conform to the cavity. The control circuitry is configured to control the supply power from the battery 116 to the electric heater 122.

Figure 3A:
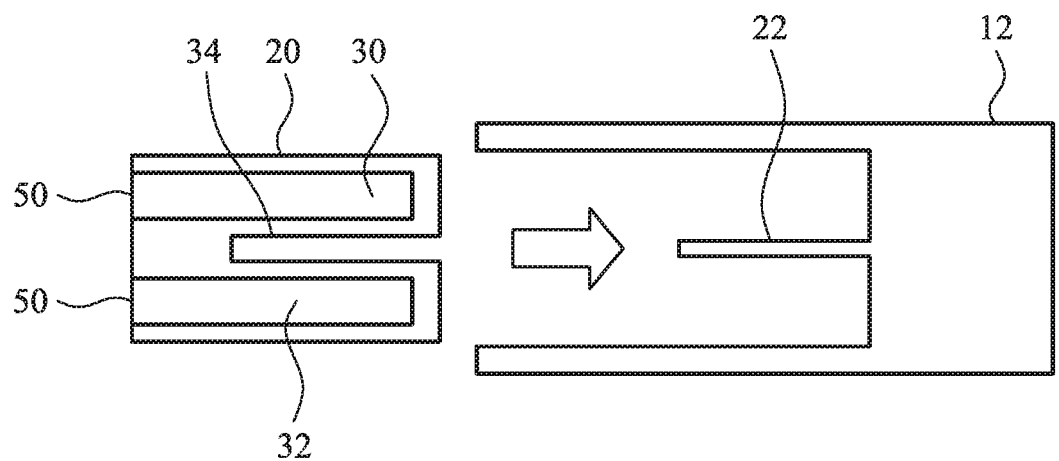
FIGS. 3a, 3b, and 3c illustrate a sequence including an insertion of a cartridge into a device body and a piercing of a frangible seal on the cartridge by a mouthpiece portion in accordance with an example embodiment.
Figure 3B:
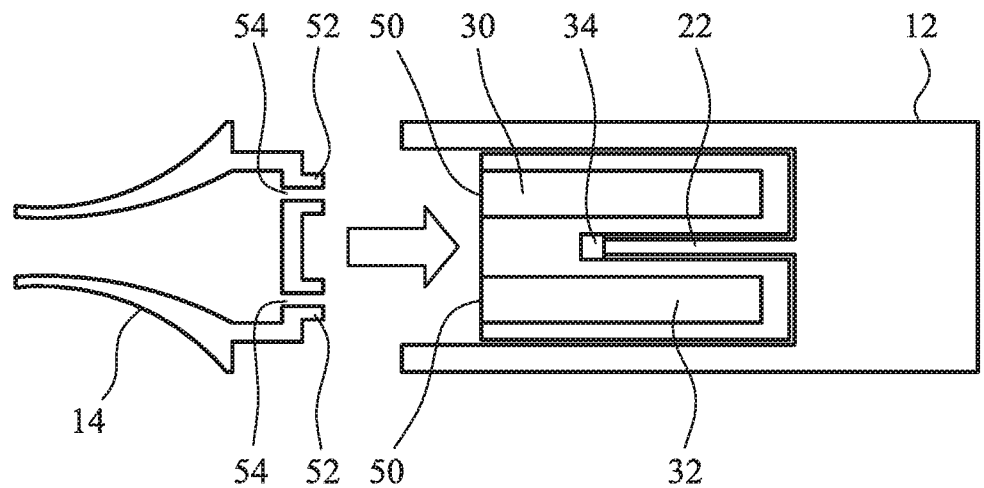
Figure 3C:
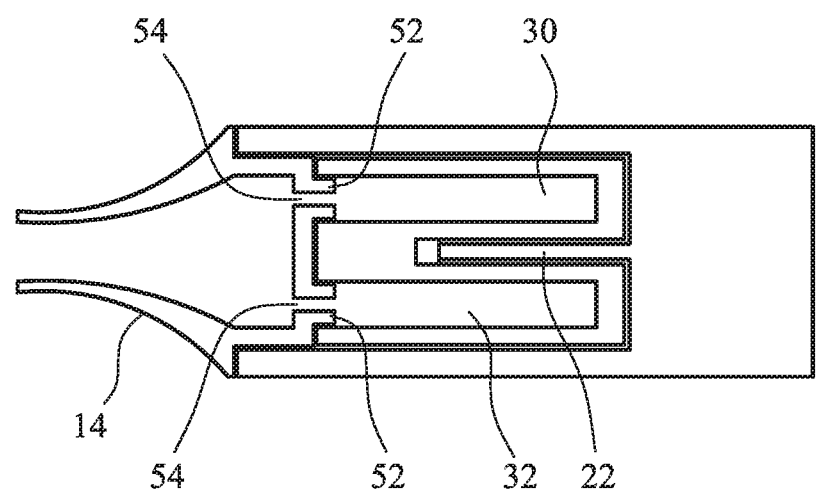

The cartridge of FIG. 4 is similar to the cartridge shown in FIG. 1. The composition of the gels in the two chambers 130 and 132 of the cartridge may be the same as in the example embodiment of FIG. 1. The cartridge housing is also formed from aluminium. However, in the example embodiment of FIG. 4, an open ended slot 134 is provided rather than a blind slot. The open ended slot 134 provides an airflow path from an air inlet 142 in the device body to the aerosol-forming chamber 140 in the mouthpiece portion 114. A cartridge piercing arrangement similar to that shown in FIG. 3 may be used to open the cartridge using the mouthpiece portion 114, with suitable adaptations made for the different airflow path. The two chambers 130 and 132 may be separate and held together as in the example embodiment of FIG. 1, or may remain separate from one another throughout their use.

In operation, the system is configured to operate in a continuous heating mode as in the example embodiment of FIG. 1. This means that the heater 122 heats the cartridge throughout an operating session rather than in response to sensed puffs. The system may be turned on using a simple switch (not shown) such that the heater heats the cartridge. A temperature sensor may be included in the system so that an indication may be provided as to when an operating temperature has been reached. The gels become a liquid upon heating above 85° C. Aerosol containing nicotine and glycerin is generated at temperatures between 180° C. to 250° C. During operation, the heater operates at approximately 250° C. The heater may operate for a fixed time period after activation (e.g., 6 minutes) or may operate until the system is switched off.

Figure 5:
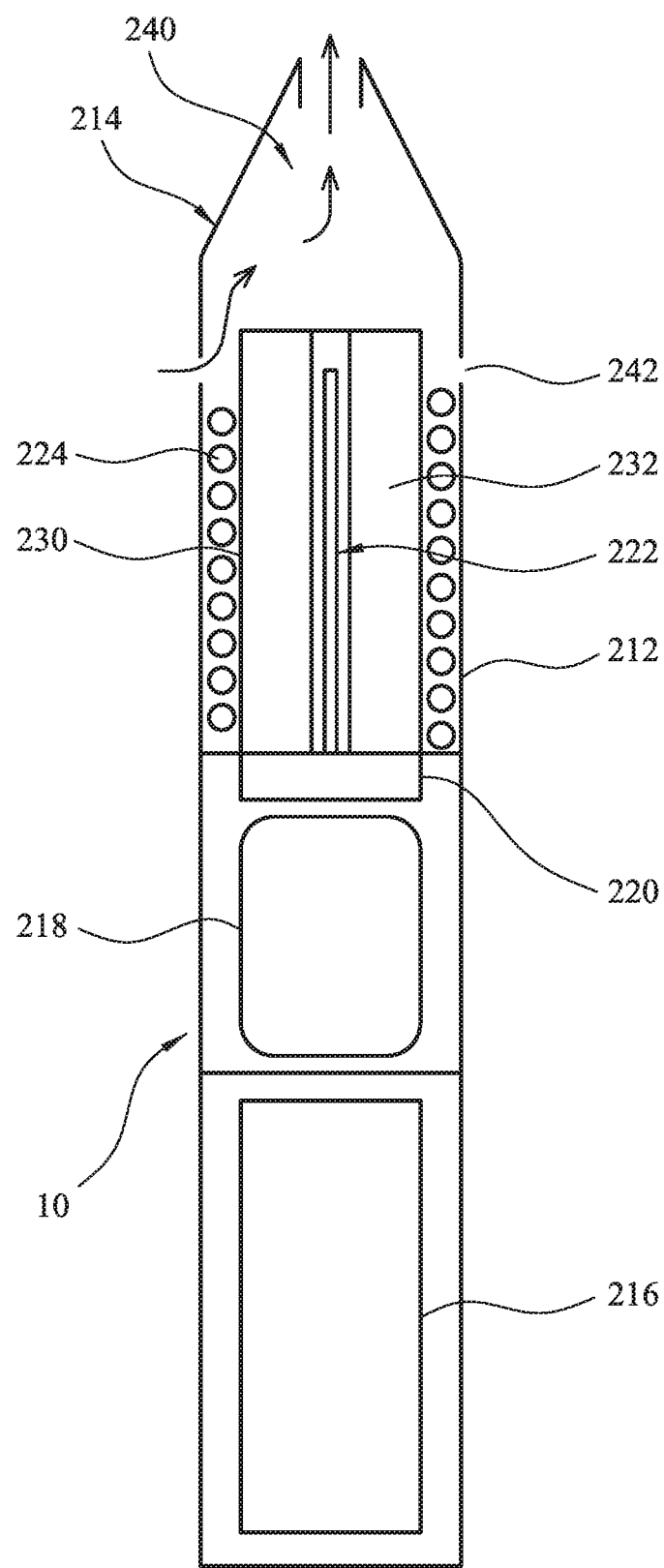
FIG. 5 is a schematic illustration of another aerosol-generating system in accordance with an example embodiment.

FIG. 5 is a schematic illustration of another aerosol-generating system in accordance with an example embodiment. The example embodiment of FIG. 5 operated by using induction heating rather than by using resistive heating. Instead of using a resistive heater either around or inside the cavity in which the cartridge is received, the device body comprises an inductor coil surrounding the cavity and a susceptor is provided in the cavity, in this example as part of the cartridge.

The device body 212 comprises a power supply, which may be a battery 216 (e.g., lithium ion battery) and electronic control circuitry 218. The device body also includes an induction coil 224, which extends around a cavity in the housing of the device body. The device body also comprises electronic circuitry 220 to generate an AC signal which is provided to the induction coil 224.

The mouthpiece portion 214 is similar to the mouthpiece portion shown in FIG. 1 and encloses an aerosol-forming chamber 240. In this example air inlets 242 are provided at the junction of the mouthpiece portion and the device body.

The cartridge of FIG. 4 is similar to the cartridge shown in FIG. 1. The composition of the gels in the two chambers of the cartridge may be the same as in the example embodiment of FIG. 1. However, rather than having a blind cavity for receiving a heater, the adjacent walls of the two chambers comprise a susceptor material 222 that heats up in the alternating magnetic field, such as a layer of iron. The susceptor material in this example is provided as part of the cartridge rather than part of the device body, but it is possible for the susceptor material to be provided as part of the device body or both in the cartridge and the device body. The entire cartridge housing may be formed from a susceptor material, or a susceptor material may be provided as a coating on one of more surfaces of the cartridge. It is also possible to provide susceptor material within the first and second chambers, suspended in the gel or other material contained there.

A sealing element is provided to seal the first and second chambers in the same manner as described with reference to FIG. 1. A cartridge piercing arrangement similar to that shown in FIG. 3 may be used to open the cartridge using the mouthpiece portion 114, with suitable adaptations made for the different airflow path. Alternatively, a simple peelable seal may be used and a vapour permeable membrane provided across the open end of the first and second chambers 230, 232.

In operation, the system is configured to operate in a continuous heating mode as in the example embodiment of FIG. 1. This means that when the device is switched on, the device supplies an AC signal to the induction coil in order to generate an alternating magnetic field in the cavity. This induces current flow in the susceptor resulting in a heating of the susceptor. If a ferromagnetic material is used as the susceptor, hysteresis losses may also contribute to the heating. The induction coil may be described as an induction heater in this context. By controlling the magnitude and frequency of the AC signal, the temperature within the first and second chambers can be controlled. A temperature sensor may be provided within the cavity and a feedback control loop used. The induction heater may operate for a fixed time period after activation (e.g., 6 minutes) or may operate until the system is switched off.

FIG. 6a is a schematic illustration of a cartridge assembly that is held within a mouthpiece tube in accordance with an example embodiment. In the example embodiment of FIG. 6a, the cartridge 330 is held within a mouthpiece tube 300. A flow restrictor 350 and lining tubes 340, 360, 370 are also held within the mouthpiece tube. The components held within the mouthpiece tube 300 are shown in an exploded view in FIG. 6b.

The cartridge 330 is similar to the cartridge shown in FIG. 2c and comprises separate chamber housings. However, the cartridge 330 has no membrane or sealing element but includes airflow channels 335 formed in the walls of the cartridge and air inlets 334 at the top of the airflow channels to allow air into the open ends of the first and second chambers.

The mouthpiece tube is formed from cardboard and has a diameter of 6.6 mm and a length of 45 mm. Lining tubes 340 are formed from polyetheretherketone (PEEK) and are provided to prevent the cardboard mouthpiece tube from absorbing moisture from within the mouthpiece tube. The lining tubes can be made relatively thin (e.g., a thickness of 0.3 mm). A flow restrictor 350 is provided to restrict the airflow to ensure mixing of air with vapour from the cartridge and ensure the generation of an aerosol within the space following the restrictor, in lining tube 360.

Figure 7:
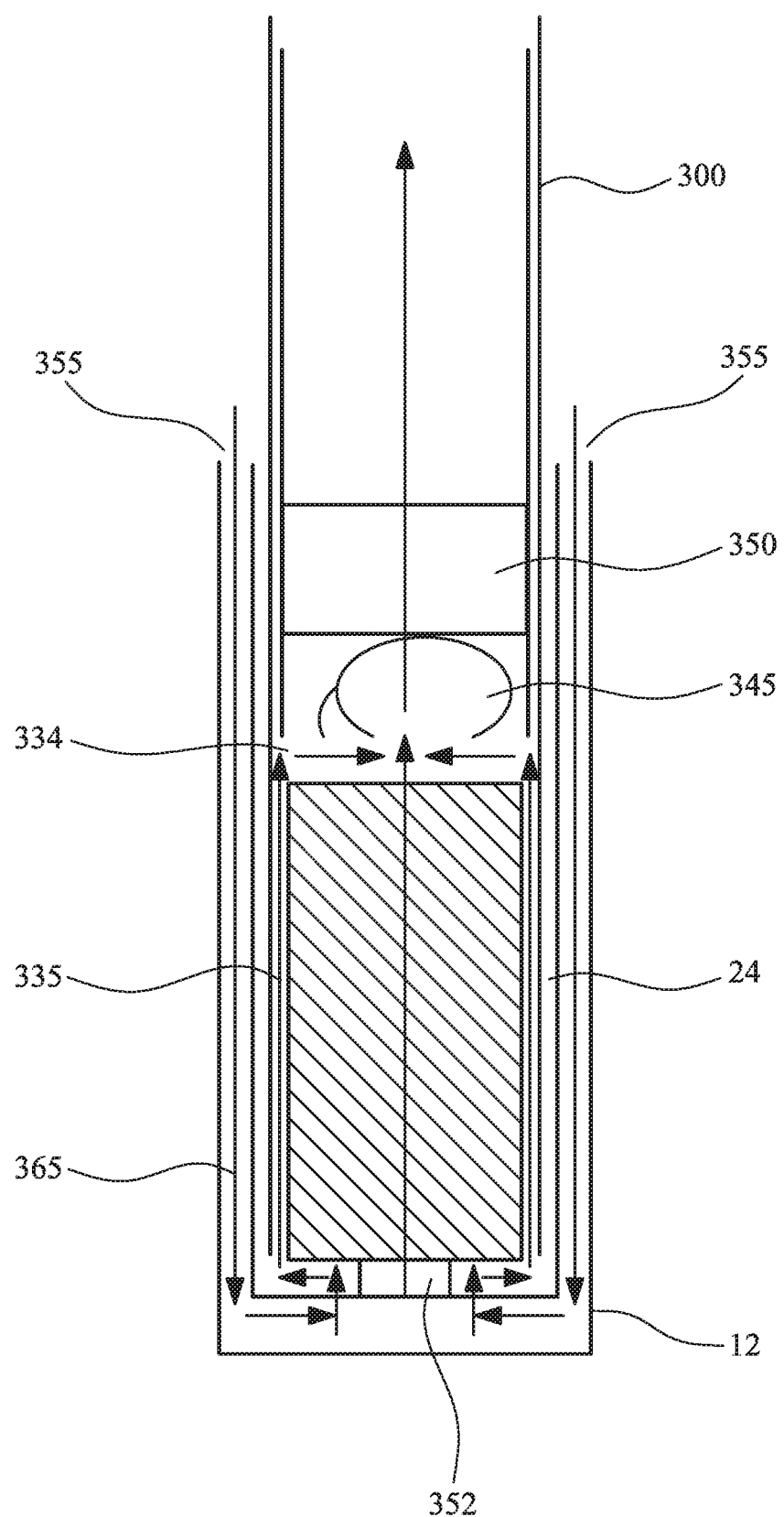

FIG. 7 illustrates the airflow within the mouthpiece tube of FIG. 6*a* during operation. The mouthpiece tube is shown within the cavity 24 of a device body 12 of the type shown in FIG. 1, but without a mouthpiece portion 14. FIG. 7 illustrates only the end of the device that receives the mouthpiece tube. The battery and control circuitry is not shown. The device includes device air inlets 355 that allow air into an internal airflow passage 365 formed in the device around the periphery of the cavity 24. A spacer element 352 is positioned in a base of the cavity to allow air to flow from the internal airflow passage 365 into the cavity 24 and then into the airflow channels 335 in the cartridge 330 and through the air inlets 334 into the interior of the mouthpiece tube.

The cartridge shown in FIGS. 6*a* and 6*b* may be heated by heater of the type shown in FIG. 1 or a type shown in FIG. 4 or 5. In operation, the system is configured to operate in a continuous heating mode as in FIG. 1. This means that the heater heats the cartridge throughout an operating session rather than in response to sensed puffs. The system may be turned on using a simple switch (not shown) such that the heater heats the cartridge. The gels in the first and second chambers become liquid upon heating and vapour containing nicotine and glycerin is generated at temperatures between 180° C. to 250° C.

When the system is at the operating temperature, an application of negative pressure on a mouth end of the mouthpiece tube will draw air through the mouthpiece tube. Air is drawn into a distal end of the mouthpiece tube, opposite the mouthpiece end from the internal airflow passage 365. The air travels up the airflow channels 335 and through air inlets 334 into space 345. The air mixes in space 345 with vapour from the first and second chambers. The mixed air and vapour then passes through the flow restrictor 350, after which it cools to continue to form an aerosol before being drawn from the system. After operation, the mouthpiece tube, including the cartridge, can be withdrawn from the device and disposed of. Mouthpiece tubes of this type may be sold in packs to provide for multiple operations of the system.

Various example embodiments have been described as configured to operate in a continuous heating scheme, in which the heater is activated for a desired or predetermined time period during which an application of a negative pressure is being applied. However, the systems described may be configured to operate in different ways. For example, power may be provided to the heater or induction coil for only the duration of each puff, based on signals from an airflow sensor within the system. Alternatively, or in addition, power to the heater or induction coil may be switched on and off in response to an actuation of a button or switch.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims. For instance, different arrangements for airflow through the system may be provided and different heating arrangements can be envisaged, such as non-electrical heaters.

The invention claimed is:

1. An aerosol-generating system comprising: a cartridge including,
   a first chamber housing defining a first airflow channel in an exterior surface of the cartridge, a first inlet downstream of the first airflow channel and in fluid communication with the first airflow channel, and a first chamber including a first open end, the first open end downstream of the first inlet, in fluid communication with the first inlet, and free of a membrane, and
   a second chamber housing defining a second airflow channel in the exterior surface of the cartridge, a second inlet downstream of the second airflow channel and in fluid communication with the second airflow channel, and a second chamber including a second open end, the second open end downstream of the second inlet, in fluid communication with the second inlet, and free of a membrane, the second chamber being separate from the first chamber, the first chamber configured to contain an aerosol-forming substrate in a form of a first gel, the second chamber configured to contain a source of a desired compound, the first chamber housing and the second chamber housing being separate or separable structures; and
   a device body configured to removably connect to the cartridge or removably receive the cartridge, the device body including,
      an electrical heater configured to heat the aerosol-forming substrate in situ to generate a vapor, the electrical heater being in indirect contact with the aerosol-forming substrate, and
      a power supply configured to apply a voltage to the electrical heater, the aerosol-generating system being free of a wick.

2. The aerosol-generating system according to claim 1, wherein the first gel includes a thermoreversible gel.

3. The aerosol-generating system according to claim 1, wherein the first chamber housing and the second chamber housing are connected by a mechanical interlock or by a fastening element.

4. The aerosol-generating system according to claim 3, wherein the first gel includes a thermoreversible gel.

5. The aerosol-generating system according to claim 3, wherein the fastening element is a ring disposed around and engaging a first portion of the first chamber housing and a second portion of the second chamber housing.

6. The aerosol-generating system according to claim 1, wherein the first gel includes agar, agarose, Gellan gum, or sodium alginate.

7. The aerosol-generating system according to claim 1, wherein the source of the desired compound includes a nicotine source or a flavour source.

8. The aerosol-generating system according to claim 1, wherein the second chamber is configured to contain a second gel, the second gel including the source of the desired compound.

9. The aerosol-generating system according to claim 1, wherein the first chamber is configured to contain a nicotine source.

10. The aerosol-generating system according to claim 1, wherein the second chamber is configured to contain a solid tobacco material.

11. The aerosol-generating system according to claim 1, wherein the first chamber housing and the second chamber housing define a slot therebetween.

12. The aerosol-generating system according to claim 11, wherein the slot is a blind slot.

13. The aerosol-generating system according to claim 12, wherein the electrical heater is positioned within the blind slot.

14. The aerosol-generating system according to claim 11, wherein the slot is an open-ended slot.

15. The aerosol-generating system according to claim 1, wherein the first chamber and the second chamber contain different compositions.

16. The aerosol-generating system according to claim 1, wherein the first chamber and the second chamber are blind chambers.

17. The aerosol-generating system according to claim 1, wherein the electric heater includes an induction heater including,
   an induction coil; and
   a susceptor.

18. The aerosol-generating system according to claim 17, wherein the susceptor is disposed within a slot defined between the first chamber housing and the second chamber housing.

19. The aerosol-generating system according to claim 17, wherein the susceptor includes a susceptor layer provided on at least one of the first chamber housing and the second chamber housing.

20. The aerosol-generating system according to claim 1, wherein the electric heater includes a resistive heater including,
   a flexible substrate, and
   an electrically-resistive track on the flexible substrate.

* * * * *